(12) United States Patent
Peel et al.

(10) Patent No.: US 10,406,391 B2
(45) Date of Patent: Sep. 10, 2019

(54) FIRESAFE COUPLING

(71) Applicant: BPR MEDICAL LIMITED, Nottinghamshire (GB)

(72) Inventors: David Edgar Peel, Nottinghamshire (GB); Richard Radford, Nottinghamshire (GB)

(73) Assignee: BPR MEDICAL LIMITED, Nottinghamshire (GB)

( * ) Notice: Subject to any disclaimer, the term of this patent is extended or adjusted under 35 U.S.C. 154(b) by 0 days.

(21) Appl. No.: 14/417,065

(22) PCT Filed: Jul. 31, 2013

(86) PCT No.: PCT/GB2013/052041
§ 371 (c)(1),
(2) Date: Jan. 23, 2015

(87) PCT Pub. No.: WO2014/020334
PCT Pub. Date: Feb. 6, 2014

(65) Prior Publication Data
US 2015/0174436 A1 Jun. 25, 2015

(30) Foreign Application Priority Data
Aug. 3, 2012 (GB) .................................. 1213928.3

(51) Int. Cl.
*F16K 17/14* (2006.01)
*A62C 4/02* (2006.01)
(Continued)

(52) U.S. Cl.
CPC ........... *A62C 4/02* (2013.01); *A61M 16/0816* (2013.01); *A61M 16/20* (2013.01);
(Continued)

(58) Field of Classification Search
CPC ............ F16L 55/1026; Y10T 137/1639; Y10T 137/1654; A62C 4/02; A61M 16/20; A61M 16/208; F16K 17/38; F16K 17/383
(Continued)

(56) References Cited

U.S. PATENT DOCUMENTS 1,022,119 A * 4/1912 Barton .................. F16K 17/383
137/75
2,707,965 A * 5/1955 Allen .................... F16K 17/383
137/539
(Continued)

FOREIGN PATENT DOCUMENTS

DE 19919700 A1 11/2000
EP 2133113 A1 12/2009
(Continued)

OTHER PUBLICATIONS

Nov. 19, 2013 International Search Report issued in International Application No. PCT/GB2013/052041.
(Continued)

*Primary Examiner* — P. Macade Nichols
(74) *Attorney, Agent, or Firm* — Kenealy Vaidya LLP

(57) ABSTRACT

The disclosed coupling can include an elongate body having an opening at each end, the openings linked by a conduit; a valve assembly located within the elongate body. The valve assembly is movable between an open position, in which gas can pass between the openings along the conduit, and a closed position in which gas flow between the openings is prevented; a biasing assembly arranged within the elongate body to move the valve assembly into the closed position; and a heat activatable stop located in the region of each opening, operable to hold the valve assembly in the open position against the biasing assembly, and adapted to release the valve assembly to allow the biasing assembly to move (Continued)

the valve assembly to the closed position at an activation temperature.

21 Claims, 1 Drawing Sheet

(51) Int. Cl.
   *F16K 17/38* (2006.01)
   *A61M 16/08* (2006.01)
   *A61M 16/20* (2006.01)
   *F16L 55/10* (2006.01)
   *A61M 16/22* (2006.01)

(52) U.S. Cl.
   CPC ........... *A61M 16/208* (2013.01); *F16K 17/38* (2013.01); *F16K 17/383* (2013.01); *F16L 55/10* (2013.01); *A61M 16/22* (2013.01); *Y10T 29/49826* (2015.01)

(58) Field of Classification Search
   USPC .................................... 137/68.14, 72, 74, 75
   See application file for complete search history.

(56) References Cited

U.S. PATENT DOCUMENTS

| 3,532,101 | A | * | 10/1970 | Snyder, Jr. ............... | F16K 17/40 |
| | | | | | 137/75 |
| 4,229,341 | A | | 10/1980 | Yamaguchi et al. | |
| 4,887,631 | A | * | 12/1989 | Friend ..................... | A62C 2/06 |
| | | | | | 137/74 |
| 4,932,431 | A | * | 6/1990 | Silagy ..................... | F16L 37/23 |
| | | | | | 137/174 |
| 2013/0186494 | A1 | * | 7/2013 | Geisel ..................... | F16L 37/23 |
| | | | | | 137/798 |

FOREIGN PATENT DOCUMENTS

| GB | 2417425 A | 3/2006 |
| GB | 2418239 A | 3/2006 |
| WO | 2008/075035 A1 | 6/2008 |

OTHER PUBLICATIONS

Nov. 30, 2012 British Search Report issued in GB Patent Application No. GB1213928.3.

* cited by examiner

FIRESAFE COUPLING

This application is a U.S. national phase filing under 35 U.S.C. § 371 of PCT Application No. PCT/GB2013/052041, filed Jul. 31, 2013, and claims priority under 35 U.S.C. § 119 to UK patent application no. 1213928.3, filed Aug. 3, 2012, the entireties of both of which are incorporated by reference herein.

FIELD OF THE INVENTION

The present invention relates to a firesafe medical gas coupling for use with flexible tubing supplying medical gas capable of combustion or of supporting combustion and a method of forming such a firesafe coupling.

BACKGROUND

Patients requiring therapeutic gas, for example, oxygen, may typically be administered that therapeutic gas via equipment such as a face mask or nasal cannula. That equipment is often connected to a gas source via flexible plastics tubing, and administration may occur in a domestic or clinical environment.

It has been established that the risk of fire when using such delivery apparatus with, for example, oxygen, oxygen enriched air, or any medical gas capable of supporting combustion, can be significant since the exposure of the apparatus to an ignition event can result in ignition. A flame which starts as an external fire supported by combustible gases leaking from delivery apparatus may then move to the interior of the flexible plastics tubing from delivery equipment and migrate rapidly upstream towards the gas source.

The fire hazard resulting from the use of such gas delivery apparatus is exacerbated in a domestic environment because the use of the oxygen is not supervised by health care workers. The presence of mandatory smoke detectors, fire alarms and other such safety equipment cannot mitigate the risks due to the rapidity of spread of a fire in, for example, an oxygen rich environment, once triggered. The risk of catastrophic fires, especially due to careless use of such apparatus is higher in the case of patients who smoke since there is a temptation for a patient to discard the oxygen delivery mask or cannula, and leave it in the vicinity, still delivering therapeutic gas, whilst a cigarette is smoked. Most oxygen delivery apparatus is set to deliver oxygen continuously at a rate determined by the needs of the patient, and removal of the delivery interface from the patient airway does not cause the delivery of oxygen to cease. In such circumstances an oxygen-enriched atmosphere can build up around the patient thereby preparing ambient surroundings for a catastrophic conflagration upon ignition.

There is therefore a need for apparatus and/or procedures to prevent or avoid fires spreading if an ignition event occurs in the proximity of the patient using combustible gas delivery equipment in a clinical or domestic environment.

SUMMARY

Accordingly, a first aspect provides a firesafe medical gas coupling for use with flexible tubing supplying medical gas capable of combustion or of supporting combustion, the coupling comprising: an elongate body having an opening in the region of each end, the openings being linked by a conduit; a valve assembly located within the elongate body, the valve assembly being movable between an open position, in which gas can pass between the openings along the conduit, and a closed position in which gas flow between the openings is prevented; a biasing assembly arranged within the elongate body to move the valve assembly into the closed position; and a heat activatable stop located in the region of each opening, operable to hold the valve assembly in the open position against the biasing assembly, and adapted to release the valve assembly to allow the biasing assembly to move the valve assembly to the closed position at an activation temperature.

The first aspect recognises that by providing an in-line device which may be installed within the flexible gas delivery tubes, for example, leading to gas delivery equipment from a source of combustible therapeutic gas, it is possible to provide a so-called "firebreak" which prevents a fire migrating to a source of gas and which serves to close off a supply of combustible gas to an existing fire, thus decreasing the chance that an environment surrounding a gas source is impregnated further with combustible gas or gas capable of supporting combustion. In the event of a fire, provision of a safety valve in a supply line may mitigate the amount of pressurized oxygen, or other gas capable of supporting combustion, available to sustain a fire.

Although it is known to provide safety valves for inserting in a gas delivery line, the first aspect recognises that such known devices are unidirectional and must be installed in such a way as to ensure they operate to arrest a fire and act as a firebreak to avoid a fire reaching a gas source. If known devices are incorrectly installed, their firebreak and fire arrest potential is reduced to zero. The first aspect seeks to address that problem by providing a safety valve which can be effectively and easily incorporated into a supply line of a gas delivery system and which it is substantially impossible to install incorrectly.

Accordingly, components of the first aspect are arranged such that a bidirectional in-line firebreak device is formed. By providing a valve assembly and biasing assembly which operates to close flow of gas through the coupling if a heat activatable stop is activated at either end or opening of the coupling, a device which operates correctly, irrespective of orientation within a supply line is provided.

In one embodiment, the elongate body comprises an externally ridged portion in the region of each end for removable connection of the coupling to the flexible tubing. It will be understood that any patient interface component of respiratory equipment, for example, a facemask or nasal cannula, is typically disposable for reasons of hygiene and thus it may be advantageous for any safety equipment associated with such respiratory equipment to be inexpensive and easy to install. It will be appreciated that a firebreak device in accordance with the first aspect installed in a gas delivery line remains accessible for checking and is easily replaceable. In some embodiments, the firesafe coupling is formed as a removable assembly having connector nozzles by which the coupling is connectable or removably connectable to a gas delivery line.

A coupling, or safety valve unit in accordance with the first aspect may be constructed in form and in material such that it does not weigh down on a supply line or pull on connections causing them to become loose, and a firesafe medical gas coupling located close to a mask or nasal cannula, if manufactured appropriately, may be such that it does not cause the patient undue discomfort due to its weight. In some embodiments, the firesafe medical gas coupling according to the first aspect is formed from an appropriate plastics material. Plastics materials may be easily formed and thus can be inexpensively produced.

Furthermore, choice of an appropriate plastics material may ensure that the device is firesafe In one embodiment, the elongate body comprises a hollow bulbous portion disposed between the externally ridged portions. Accordingly, mechanisms and components of the valve assembly and biasing assembly may be housed within the hollow bulbous portion of the elongate body. The bulbous portion may be positioned midway between the ends of the elongate portion. That is to say the bulbous portion may be centrally located between the ends of the elongate portion.

In one embodiment, the biasing assembly is housed in the hollow bulbous portion. In some embodiments, the mechanism required to urge the valve assembly into a closed position may be housed substantially centrally within the elongate body. Housing the mechanism within the bulbous portion may allow for necessary components of the biasing assembly to be housed within the coupling without causing the flow of gas through the coupling to be significantly reduced, thus mitigating the impact of installing a firesafe coupling in flexible tubing coupled to a therapeutic gas supply.

In one embodiment, the hollow bulbous portion is integrally formed with at least one of the externally ridged portions. Accordingly, in order to construct a coupling in accordance with the first aspect, one of the end portions, in some embodiments including external ridges to allow for a gas tight, friction fit of said coupling to flexible plastics supply tubing used to deliver gas, may be integrally formed with the hollow bulbous portion, then valve apparatus and biasing apparatus assembled before a second end portion is connected to the hollow bulbous portion. In some embodiments, the hollow bulbous portion may be formed separately to the end portions. In such embodiments, the end portions may be affixed, for example, via a snap fit, or screw mechanism, to the hollow bulbous portion after the valve assembly and biasing assembly have been arranged within the component pieces of the elongate body.

In one embodiment, the biasing assembly is operable to move the valve assembly towards the opening at which the heat activatable stop has reached the activation temperature. Accordingly, the biasing apparatus in some embodiments may be operable to exert a biasing force from the centre of the elongate body towards each end opening simultaneously. In some embodiments, when one activatable stop has been activated, the other retains the valve apparatus such that the non-activated stop opening remains open, the valve apparatus sealing the conduit as a result of the activated stop no longer holding the valve apparatus in the open position.

In one embodiment, the valve assembly is substantially symmetrically arranged about the biasing assembly within the elongate body. Accordingly, it will be understood that the biasing apparatus and valve apparatus may comprise a pair of substantially diametrically arranged mechanisms. Each may operate substantially independently of the other.

In one embodiment, the valve assembly comprises: a valve foot arranged to engage the heat activatable stop. In one embodiment, the foot comprises at least one lateral protrusion. The foot may comprise at least one lateral protrusion. However, the foot may comprise two or more lateral protrusions, which are preferably diametrically opposed across a plane of symmetry of the elongate link member.

In one embodiment, the valve assembly comprises: a valve head arranged to form a seal between the valve head and a wall of the conduit when the valve assembly is in the closed position. Accordingly, the valve head may press against a wall of the conduit to form a gas tight, fire safe seal. In one embodiment, at least a portion of the surface of the valve head is formed of a sealing material. In one embodiment, the valve head comprises an annular recess and an annular sealing member disposed therein, to form a seal between the valve head and a wall of the conduit when the valve assembly is in the closed position.

The sealing member and the valve head may be arranged to co-operate such that the sealing member seals against the wall of the conduit when the valve apparatus is in the closed position. The sealing member may take, for example, the form of a substantially spherical ball element, and the valve head may be shaped to seat the sealing member. Alternatively, the valve head may have an annular recess and an annular sealing member disposed therein to form a seal between the valve head and the wall of the conduit when the valve member is in the valve closure position.

At least a portion of the surface of the valve head may be formed of a suitable material, to form a seal between the valve head and the wall of the conduit when the valve apparatus is in the closed position. The whole of the head itself may be formed from such a material. Alternatively, the sealing member may be formed of a suitable material to form a seal against the wall of the conduit when the valve apparatus is in the closed position.

The valve apparatus may be resiliently-biased by one or more coiled compression springs mounted within, for example, the bulbous hollow body of the elongate body, arranged to be compressed between an internal rim provided by an internal wall of the conduit and shoulder provided on the valve apparatus, for example, the valve head. The internal rim and shoulder may be substantially annular.

In one embodiment, the valve assembly further comprises an elongate link member extending from the valve head to the foot. In one embodiment, a fluid flow path is defined between the elongate link member and a wall of the conduit. In one embodiment, the elongate link member comprises a generally laminar elongate element. In one embodiment, the elongate link member comprises a tapered elongate element. Accordingly, the valve apparatus and in particular, the elongate link member may be formed to disrupt a flow of therapeutic gas through the firesafe coupling as little as possible.

In one embodiment, the valve head is integrally formed with the elongate link member and the foot. Accordingly, the valve member may be moulded or formed from a plastics material.

The thermally activatable stop may comprise an inwardly directed annular flange arranged to retain the foot (or feet) of the valve apparatus within the elongate body. The thermally activatable stop, or thermally fusible portion, of the coupling may be formed from a heat susceptible material, which may be selected from thermoplastic materials, solder and waxes. In some embodiments the thermally activatable stop is formed from a thermoplastic material, such as, for example, Polyvinylchloride (PVC).

A second aspect provides a method of forming a firesafe medical gas coupling for use with flexible tubing supplying medical gas capable of combustion or of supporting combustion, the method comprising: providing an elongate body having an opening in the region of each end, the openings being linked by a conduit; locating a valve assembly within the elongate body, the valve assembly being movable between an open position, in which gas can pass between the openings along the conduit, and a closed position in which gas flow between the openings is prevented; arranging a biasing assembly within the elongate body to move the valve assembly into the closed position; and locating a heat activatable stop in the region of each opening, operable to hold the valve assembly in the open position against the biasing assembly, and adapted to release the valve assembly to allow the biasing assembly to move the valve assembly to the closed position at an activation temperature.

In one embodiment, the elongate body comprises an externally ridged portion in the region of each end for removable connection of the coupling to the flexible tubing.

In one embodiment, the method comprises disposing a hollow bulbous portion between the externally ridged portions to form the elongate body.

In one embodiment, the method comprises housing the biasing assembly in the hollow bulbous portion.

In one embodiment, the method comprises integrally forming the hollow bulbous portion with at least one of the externally ridged portions.

In one embodiment, the biasing assembly is arranged to be operable to move the valve assembly towards the opening at which the heat activatable stop has reached the activation temperature.

In one embodiment, the method comprises substantially symmetrically arranging the valve assembly about the biasing assembly within the elongate body.

In one embodiment, the valve assembly comprises: a valve foot arranged to engage the heat activatable stop.

In one embodiment, the foot comprises at least one lateral protrusion.

In one embodiment, the valve assembly comprises: a valve head arranged to form a seal between the valve head and a wall of the conduit when the valve assembly is in the closed position.

In one embodiment, the method comprises forming at least a portion of the surface of the valve head of a sealing material.

In one embodiment, the valve head comprises an annular recess and an annular sealing member disposed therein, to form a seal between the valve head and a wall of the conduit when the valve assembly is in the closed position.

In one embodiment, the valve assembly further comprises an elongate link member extending from the valve head to the foot.

In one embodiment, a fluid flow path is defined between the elongate link member and a wall of the conduit.

In one embodiment, the elongate link member comprises a generally laminar elongate element.

In one embodiment, the elongate link member comprises a tapered elongate element.

In one embodiment, the valve head is integrally formed with the elongate link member and the foot.

Further particular and preferred aspects are set out in the accompanying independent and dependent claims. Features of the dependent claims may be combined with features of the independent claims as appropriate, and in combinations other than those explicitly set out in the claims.

Where an apparatus feature is described as being operable to provide a function, it will be appreciated that this includes an apparatus feature which provides that function or which is adapted or configured to provide that function.

BRIEF DESCRIPTION OF THE DRAWINGS

Embodiments of the present invention will now be described further, with reference to the accompanying drawings, in which.

DESCRIPTION OF THE EMBODIMENTS

Patients requiring therapeutic gas, for example, oxygen, may typically be administered that therapeutic gas via equipment such as a face mask or nasal cannula. That equipment is often connected to a gas source via flexible plastics tubing, and administration may occur in a domestic or clinical environment.

A therapeutic gas supply line from a gas source to a patient typically comprises flexible plastics tubing, for example, polythene or a similar plastics material.

Figure 1:
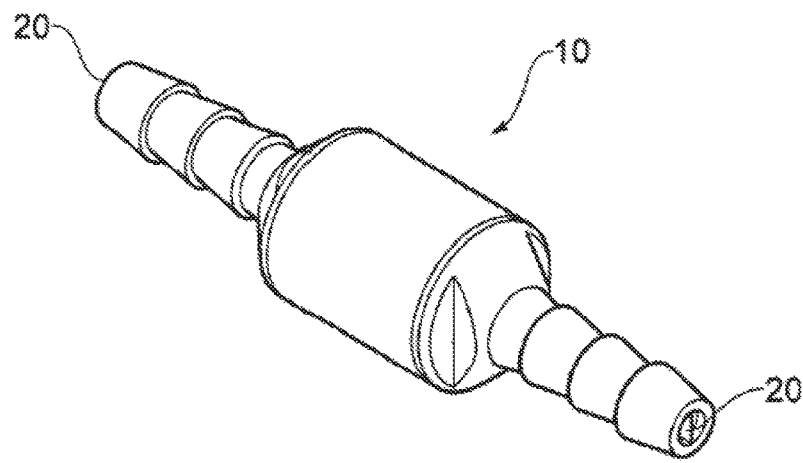
FIG. 1 is a perspective view of a firesafe coupling according to one embodiment.

FIG. 1 is a perspective view of a firesafe coupling according to one embodiment, suitable for insertion into a typical gas supply line. The firesafe medical gas coupling 10 shown in FIG. 1 is suitable for use with flexible tubing supplying medical gas capable of combustion or of supporting combustion. The coupling 10 comprises generally: an elongate body having an opening 20 in the region of each end. Those openings are linked by a conduit 30 (not shown in FIG. 1). A valve assembly is located within the elongate body. The valve assembly is movable between an open position, in which gas can pass between the openings 20 along said conduit, and a closed position in which gas flow between the openings is prevented. The coupling 10 also comprises a biasing assembly arranged within the elongate body to move the valve assembly into the closed position. The coupling also includes a heat activatable stop located in the region of each opening 20. The heat activatable stop is operable to hold the valve assembly in the open position against the biasing assembly and is arranged to release the valve assembly to allow the biasing assembly to move the valve assembly to the closed position at a preselected activation temperature.

Figure 2:
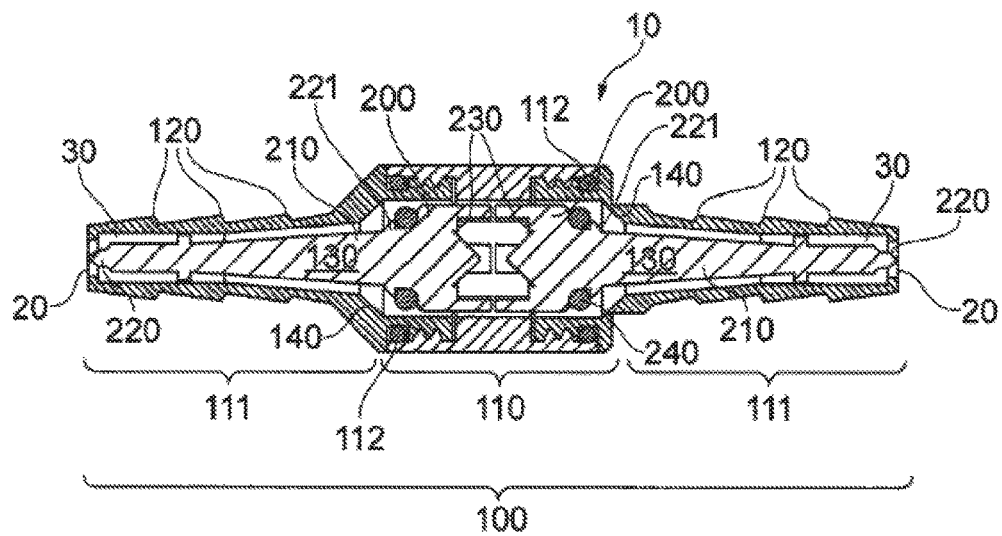
FIG. 2 is an axial section through the firesafe coupling of FIG. 1.

FIG. 2 shows an exemplary interior structure of a firesafe coupling such as that shown in FIG. 1. It is to be understood, however, that other interior configurations of a firesafe coupling are possible.

In the arrangement shown in FIG. 2, the coupling 10 shown comprises an elongate body 100, formed from a hollow bulbous central portion 110 from which projects, in an axial direction, a nozzle portion 111. The nozzle portions are arranged to screw into the hollow bulbous central portion 110. In order to ensure such joins are gas tight, a sealing ring 112 may be provided. Such a sealing ring 112 may be formed from an appropriate sealing material, for example, rubber, and may be substantially annular. The screw fixing, comprising a cooperating screw and thread portion provided on the central portion 110 and nozzle portions 111 may compress the sealing ring 112.

In the exemplary configuration shown in FIG. 2, each nozzle portion 111 forming part of the elongate body 100 has external ridges 120 for engagement with an interior surface of flexible tubing.

At the end of each nozzle portion 111 there is provided an opening 20. The openings 20 are linked via a conduit 30, which passes along the length of the elongate body 100 and through which gas may flow when the coupling is in position in a gas supply line and whilst the valve assembly described in detail below is in the open position.

The central hollow portion 110 houses one or more springs (not shown for reasons of clarity) which act upon valve apparatus 130 mounted within the elongate body 100. In the arrangement shown in FIG. 2, the valve apparatus 130 comprises two substantially identical halves, symmetrically arranged within the elongate body. Each half of the valve apparatus comprises a head 200 integrally formed with an elongate link member 210 which extends through the conduit 30 along the nozzle portion of the elongate body 111 and terminates in a foot 220. The elongate link member 210 takes the form of a generally tapered stem.

The head 200 in the embodiment shown has a shoulder portion 230 against which the spring or springs exerts a force to urge the valve assembly into a closed position. The head also has a conically tapering neck portion 221, shaped to correspond with an annular valve seat (shoulder) 140 formed on an internal surface of the hollow bulbous portion of elongate body 100. The head 200 has an annular recess defined between the head 200 and the elongate link member 210 the recess accommodates a resilient sealing O-ring 240. The internal surface of the bulbous portion 110 defines the annular shoulder 140 which is of generally frusto-conical form. The tapered annular shoulder 220 of the valve apparatus and in particular, the resilient sealing O-ring 240 seals against annular shoulder 140 in the event that a thermally activated stop, described below, is activated due to exposure to excessive heat, for example, due to fire or explosion in its vicinity.

In some embodiments, the foot 220 of the elongate link member 210 bears against a rim or inwardly projecting lip provided in the region of the openings 20. The combination of the foot and the lip acts as a thermally fusible stop to retain the valve apparatus in an open position, working against the spring or springs provided to urge the valve apparatus into a closed position.

In some embodiments, the foot 220 of the elongate link member 210 bears against a thermally fusible stop which acts as a retaining member. The stop takes the form of a collar which is mounted at the exit end, in the region of openings 20 of the nozzle portions 111. The collar may be inserted into the nozzle portion 111 and form a snap fit with a rim recess provided on an inside surface of the nozzle portion. The collar can provide a radially inwardly extending shoulder or rim against which the foot bears to retain the valve apparatus in an open position, working against the spring or springs provided to urge the valve apparatus into a closed position.

According to the first embodiment, the inwardly projecting lip and/or foot may be formed of a material which is sensitive to heat and softens or fuses at the temperatures such as may be caused by flashback and/or ignition of a gas. That material must also have sufficient strength that, in use, it retains its structural integrity within the exit end of the nozzle section 111 against the compressive force of the spring or springs acting thereon. Suitable materials include some thermoplastics such as, for example, Polyvinylchloride (PVC), and materials such as waxes and lead free solder.

According to the second embodiment, the collar is formed of a material which is sensitive to heat and softens or fuses at the temperatures such as may be caused by flashback and/or ignition of a gas. That material must also have sufficient strength that, in use, it retains its structural integrity within the exit end of the nozzle section 111 against the compressive force of the spring or springs acting thereon. Suitable materials include some thermoplastics such as, for example, Polyvinylchloride (PVC), and materials such as waxes and lead free solder.

The firesafe coupling of aspects and embodiments described herein may be fitted in a gas circuit formed between a pressurised gas supply such as that commonly used in the home for those requiring oxygen to assist a patient's breathing, and a respiratory support device, such as a mask or nasal cannula. The gas supply may be in the form of an oxygen cylinder which provides oxygen for enrichment of normal oxygen intake by admixture with ambient air, or may be in the form of a source of oxygen-enriched air, both being under pressure. The pressure of the supply to the patient is regulated by suitable pressure regulators. The firesafe coupling according to aspects and embodiments is positioned so as to ensure that in the event of the oxygen or oxygen-enriched air igniting, the supply thereof can be cut off quickly. It will be understood that if the thermally activatable stop softens as a result of increased temperature it weakens sufficiently such that it no longer resists the biasing force of biasing apparatus to hold the valve apparatus in an open position and the spring(s) provided overcome resistance offered by the thermally activatable stop, thereby allowing movement of the valve apparatus to urge the sealing ring 240 against the annular shoulder 140 formed on the inner surface of the elongate body, thereby closing the valve provided as part of the firesafe coupling.

Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents.

The invention claimed is:

1. A firesafe medical gas coupling for use with medical gas capable of combustion or of supporting combustion, the coupling comprising:
   an elongate body having an opening in a region of each end, the openings being linked by a conduit;
   a valve assembly located within the elongate body, the valve assembly being movable between an open position, in which gas can pass between the openings along the conduit, and a closed position in which gas flow between the openings is prevented; the valve assembly comprising a first and second valve member; an elongate link member;
   a biasing assembly arranged within the elongate body to move the valve assembly into the closed position; and
   a heat activatable stop located between the biasing assembly and the region of each end of the elongate body, the heat activatable stop including a first inwardly projecting annular flange located between the biasing assembly and the region of the opening at one end, the heat activatable stop also including a second inwardly projecting annular flange located between the biasing assembly and the region of the opening at the other end, each annular flange being operable as a thermally fusable stop to hold the valve assembly in the open position against the biasing assembly, and adapted to release the valve assembly to allow the biasing assembly to move the valve assembly to the closed position at an activation temperature, to close flow of gas through the coupling if the heat activatable stop is activated at either end of the coupling, the heat activatable stop being formed from a material which is sensitive to heat and softens or fuses on exposure to temperatures caused by flashback or ignition of the medical gas capable of combustion or of supporting combustion, the material forming the heat activatable stop softens or fuses upon being exposed to an activation temperature over a period of a few seconds to be sufficiently softened or fused and thereby enable the biasing assembly to move the valve assembly to the closed position to close flow of gas through the coupling.

2. The firesafe coupling according to claim 1, wherein the valve assembly is substantially symmetrically arranged about the biasing assembly within the elongate body.

3. The firesafe coupling according to claim 1, wherein the biasing assembly is operable to move the valve assembly towards the opening at which the heat activatable stop has reached the activation temperature.

4. The firesafe coupling according to claim 1, wherein the elongate body comprises an externally ridged portion in the region of each end for removable connection of the coupling to flexible tubing.

5. The firesafe coupling according to claim 4, wherein the elongate body comprises a hollow bulbous portion disposed between the externally ridged portions.

6. The firesafe coupling according to claim 5, wherein the biasing assembly is housed in the hollow bulbous portion.

7. The firesafe coupling according to claim 5, wherein the hollow bulbous portion is integrally formed with at least one of the externally ridged portions.

8. The firesafe coupling according to claim 1, wherein the valve assembly comprises:
a valve foot arranged to engage the heat activatable stop.

9. The firesafe coupling according to claim 1, wherein the valve assembly comprises a valve foot, the valve foot forming at least part of the heat activatable stop.

10. The firesafe coupling according to claim 8, wherein the foot comprises at least one lateral protrusion.

11. The firesafe coupling according claim 1, wherein the valve assembly comprises:
a valve head arranged to form a seal between the valve head and a wall of the conduit when the valve assembly is in the closed position.

12. The firesafe coupling according to claim 11, wherein at least a portion of a surface of the valve head is formed of a sealing material.

13. The firesafe coupling according to claim 11, wherein the valve head comprises an annular recess and an annular sealing member disposed therein, to form a seal between the valve head and a wall of the conduit when the valve assembly is in the closed position.

14. The firesafe coupling according to claim 11, wherein the valve assembly further comprises an elongate link member extending from the valve head to a valve foot.

15. The firesafe coupling according to claim 14, wherein a fluid flow path is defined between the elongate link member and a wall of the conduit.

16. The firesafe coupling according to claim 14, wherein the elongate link member comprises a generally laminar elongate element.

17. The firesafe coupling according to claim 14, wherein the elongate link member comprises a tapered elongate element.

18. The firesafe coupling according to claim 11, wherein the valve head is integrally formed with an elongate link member and a foot.

19. A method of forming a firesafe medical gas coupling for use with medical gas capable of combustion or of supporting combustion, the method comprising:
providing an elongate body having an opening in a region of each end, the openings being linked by a conduit;
locating a valve assembly within the elongate body, the valve assembly being movable between an open position, in which gas can pass between the openings along the conduit, and a closed position in which gas flow between the openings is prevented; the valve assembly comprising a first and second valve member; an elongate link member;
arranging a biasing assembly within the elongate body to move the valve assembly into the closed position; and
locating a heat activatable stop located between the biasing assembly and the region of each end of the elongate body, the heat activatable stop including a first inwardly projecting annular flange located between the biasing assembly and the region of the opening at one end, the heat activatable stop also including a second inwardly projecting annular flange located between the biasing assembly and the region of the opening at the other end, each annular flange being operable as a thermally fusable stop to hold the valve assembly in the open position against the biasing assembly, and adapted to release the valve assembly to allow the biasing assembly to move the valve assembly to the closed position at an activation temperature, to close flow of gas through the coupling if the heat activatable stop is activated at either end of the coupling, the heat activatable stop being formed from a material which is sensitive to heat and softens or fuses on exposure to temperatures caused by flashback or ignition of the medical gas capable of combustion or of supporting combustion, the material forming the heat activatable stop softens or fuses upon being exposed to an activation temperature over a period of a few seconds to be sufficiently softened or fused and thereby enable the biasing assembly to move the valve assembly to the closed position to close flow of gas through the coupling.

20. A firesafe medical gas coupling for use with flexible tubing supplying medical gas capable of combustion or of supporting combustion, said coupling comprising:
an elongate body having an opening in the region of each end, said openings being linked by a conduit;
a valve assembly located within said elongate body, said valve assembly being movable between an open position, in which gas can pass between said openings along said conduit, and a closed position in which gas flow between said openings is prevented; the valve assembly comprising a first and second valve member; an elongate link member;
a biasing assembly arranged within said elongate body to move said valve assembly into said closed position; and
a heat activatable stop located in the region of each said opening and integrally formed with said elongate body, operable to hold said valve assembly in said open position against said biasing assembly, and adapted to release said valve assembly to allow said biasing assembly to move said valve assembly to said closed position at an activation temperature, the heat activatable stop being formed from a material which is sensitive to heat and softens or fuses on exposure to temperatures caused by flashback or ignition of the medical gas capable of combustion or of supporting combustion, the material forming the heat activatable stop softens or fuses upon being exposed to an activation temperature over a period of a few seconds to be sufficiently softened or fused and thereby enable the biasing assembly to move the valve assembly to the closed position to close flow of gas through the coupling.

21. A method of forming a firesafe medical gas coupling for use with medical gas capable of combustion or of supporting combustion, the method comprising:

providing an elongate body having an opening in a region of each end, the openings being linked by a conduit;

locating a valve assembly within the elongate body, the valve assembly being movable between an open position, in which gas can pass between the openings along the conduit, and a closed position in which gas flow between the openings is prevented; the valve assembly comprising a first and second valve member; an elongate link member;

arranging a biasing assembly within the elongate body to move the valve assembly into the closed position; and locating a heat activatable stop located between the biasing assembly and the region of each end of the elongate body, the heat activatable stop being integrally formed with said elongate body, operable to hold said valve assembly in said open position against said biasing assembly, and adapted to release said valve assembly to allow said biasing assembly to move said valve assembly to said closed position at an activation temperature, the heat activatable stop being formed from a material which is sensitive to heat and softens or fuses on exposure to temperatures caused by flashback or ignition of the medical gas capable of combustion or of supporting combustion, the material forming the heat activatable stop softens or fuses upon being exposed to an activation temperature over a period of a few seconds to be sufficiently softened or fused and thereby enable the biasing assembly to move the valve assembly to the closed position to close flow of gas through the coupling.

* * * * *